US010028957B2

(12) United States Patent
Wright et al.

(10) Patent No.: US 10,028,957 B2
(45) Date of Patent: Jul. 24, 2018

(54) DEPOT FORMULATIONS

(71) Applicant: DURECT CORPORATION, Cupertino, CA (US)

(72) Inventors: Jeremy C. Wright, Los Altos, CA (US); Felix Theeuwes, Los Altos Hills, CA (US); John W. Gibson, Springville, AL (US); Keith E. Branham, Pelham, AL (US); Stefania Sjobeck, Astorp (SE)

(73) Assignee: DURECT CORPORATION, Cupertino, CA (US)

( * ) Notice: Subject to any disclaimer, the term of this patent is extended or adjusted under 35 U.S.C. 154(b) by 666 days.

(21) Appl. No.: 13/790,902

(22) Filed: Mar. 8, 2013

(65) Prior Publication Data

US 2013/0289053 A1 Oct. 31, 2013

Related U.S. Application Data

(63) Continuation of application No. 12/152,764, filed on May 16, 2008.

(60) Provisional application No. 60/930,739, filed on May 18, 2007.

(51) Int. Cl.
| | |
|---|---|
| *A61K 31/519* | (2006.01) |
| *A61K 47/22* | (2006.01) |
| *A61K 47/34* | (2017.01) |
| *A61K 47/26* | (2006.01) |
| *A61K 9/00* | (2006.01) |
| *A61K 9/10* | (2006.01) |
| *A61K 9/08* | (2006.01) |

(52) U.S. Cl.
CPC .......... *A61K 31/519* (2013.01); *A61K 9/0019* (2013.01); *A61K 9/0024* (2013.01); *A61K 9/08* (2013.01); *A61K 9/10* (2013.01); *A61K 47/22* (2013.01); *A61K 47/26* (2013.01); *A61K 47/34* (2013.01)

(58) Field of Classification Search
None
See application file for complete search history.

(56) References Cited

U.S. PATENT DOCUMENTS

| | | |
|---|---|---|
| 4,530,840 A | 7/1985 | Tice et al. |
| 4,622,219 A | 11/1986 | Haynes |
| 4,725,442 A | 2/1988 | Haynes |
| 4,767,628 A | 8/1988 | Hutchinson |
| 4,891,225 A | 1/1990 | Langer |
| 4,906,474 A | 3/1990 | Langer |
| 4,938,763 A | 7/1990 | Dunn et al. |
| 4,957,744 A | 9/1990 | Della Valle et al. |
| 5,149,543 A | 9/1992 | Cohen et al. |
| 5,534,269 A | 7/1996 | Igari et al. |
| 5,643,605 A * | 7/1997 | Cleland et al. ............... 424/489 |
| 5,747,058 A | 5/1998 | Tipton et al. |
| 5,968,542 A | 10/1999 | Tipton |
| 6,130,200 A | 10/2000 | Brodbeck et al. |
| 6,291,013 B1 | 9/2001 | Gibson et al. |
| 6,331,311 B1 | 12/2001 | Brodbeck et al. |
| 6,413,536 B1 | 7/2002 | Gibson et al. |
| 6,468,961 B1 | 10/2002 | Brodbeck et al. |
| 6,673,767 B1 | 10/2004 | Brodbeck et al. |
| 6,956,059 B2 | 10/2005 | Coupland |
| 7,833,543 B2 | 11/2010 | Gibson et al. |
| 8,133,507 B2 | 3/2012 | Yum et al. |
| 2002/0064547 A1 | 5/2002 | Chern et al. |
| 2003/0009145 A1 | 1/2003 | Struijker-Boudier et al. |
| 2004/0018238 A1 | 1/2004 | Shukla |
| 2004/0101557 A1 | 5/2004 | Gibson et al. |
| 2004/0258731 A1 | 5/2004 | Yoshiki et al. |
| 2007/0077304 A1 | 4/2007 | Luk et al. |
| 2007/0108405 A1 | 5/2007 | Khoo et al. |
| 2007/0196416 A1 | 8/2007 | Chien et al. |
| 2008/0287464 A1 | 11/2008 | Wright et al. |
| 2014/0308352 A1 | 10/2014 | Wright et al. |

FOREIGN PATENT DOCUMENTS

| | | |
|---|---|---|
| EP | 0998917 | 5/2000 |
| EP | 1210942 | 6/2002 |
| EP | 1649850 | 4/2006 |
| EP | 2361609 | 7/2013 |
| WO | 98/27963 | 7/1998 |
| WO | 2000/24374 | 10/1998 |
| WO | 00/24374 | 5/2000 |
| WO | 02/00137 | 1/2002 |
| WO | 02/076344 | 10/2002 |
| WO | 2003/041684 | 5/2003 |

(Continued)

OTHER PUBLICATIONS

Middleton et al. MDDI Medical Device and Diagnostic Industry News Products and Suppliers 1998.*
Lambert et al. Journal of Controlled Release 1995 33:189-195.
Ravivarapu et al. Journal of Pharmaceutical Science 89:732-741.
Dong et al., "[Development of Injectable Biodegradable in-situ Forming Gel Implants]," [Progress in Pharmaceutical Sciences], 31:109-113.
Carraway KM, Meador SK, Sullivan SA, Gibson JW, Tipton AJ, Drug Release From a Controlled Release Aerosol: Effects of Formulation Variables, Southern BioSystems, Inc., Birmingham, ALAAPS Indianapolis Nov. 2000.
Desai et al., "Surface modification of polymer biomaterials for reduced thrombogenicity, " Polym. Mater. Sci. Eng. 62:731-735, 1991.

(Continued)

*Primary Examiner* — Robert A Wax
*Assistant Examiner* — Caralynne E Helm
(74) *Attorney, Agent, or Firm* — Greenblum & Bernstein, P.L.C.

(57) ABSTRACT

Disclosed are formulations and related methods that comprise a non-polymeric, non-water soluble high viscosity liquid carrier material having a viscosity of at least 5,000 cP at 37° C. that does not crystallize neat under ambient or physiological conditions; a specified linear polymer comprising lactide repeat units; and one or more solvents that have a solvent capacity.

27 Claims, No Drawings

(56) References Cited

FOREIGN PATENT DOCUMENTS

| WO | 2003/041685 | 5/2003 |
| --- | --- | --- |
| WO | 2003/041757 | 5/2003 |
| WO | 2004/000269 | 12/2003 |
| WO | 2004/000395 | 12/2003 |
| WO | 2004/011054 | 2/2004 |
| WO | 2004/011065 | 2/2004 |
| WO | 2004/043432 | 5/2004 |
| WO | 04/026357 | 9/2004 |
| WO | 2005/048989 | 6/2005 |
| WO | 2005/089670 | 9/2005 |
| WO | 2007/084460 | 1/2007 |
| WO | 2009/100222 | 2/2009 |

OTHER PUBLICATIONS

Eliaz et al., Characterization of a polymeric PLGA-injectable implant delivery system for the controlled release of proteins, J. Biomed. Mater. Res. 2000, 50:388-396.

Johnson CA, Thompson DL, Jr., Sullivan SA, Gibson JW, Tipton AJ, Simon BW, Burns PJ, Biodegradable Delivery Systems for Estradiol: Comparison Between Poly (DL-Lactide) Microspheres and the SABER Delivery System, Proceed Int'l Symp. Control. Rel. Bioact. Mater., 26 (1999), Controlled Release Society, Inc.

Kulkarni RK et al. :Polylactic Acid for Surgical Implants, Arch. Surg. vol. 63, Nov. 1966, 839-843.

Lin et al., "A novel risperidone-loaded SAIB-PLGA mixture matrix depot with a reduced burst release: effects of solvents and PLGA on drug release behaviors in vitro/in vivo", J. Mater. Sci: Mater. Med (2010) 23: 443-455.

Sullivan SA, Meador SK, Dodson KM, Tipton AJ, Gibson JW; "Incorporation of Polymer microparticles into sucrose acetate isobutyrate reduces burst and extends release", Proceed. Int'l, Sump, Control, Rel, Bioact, Mater., 27, Controlled Release Society, Inc. (2000).

Okumu FW, Daugherty A, Dao LN, Fielder PJ, Brooks D, Sane S, Sullivan SA, Tipton AJ, Cleland JL; "Evaluation of the SABER TM Delivery system for sustained release of Growth Hormone Formulation design and in vivo assessment" 2001.

Penco M et al., "A New Chain Extension Reaction on Poly (lactic-glycolic acid) (PLGA) Thermal Oligomers Leading to High Molecular Weight PLGA-Based Polymeric Products," Polymer International 46, 203-216, 1998.

Sullivan SA, Yarbrough JC, Fengl RW, Tipton AJ, Gibson JW, sustained Release of Orally Administered Active Using SABER TM Delivery System Incorporated into Soft Gelatin Capsules, Proceed Ont'l Symp. Control Rel. Bioact. Mater., 25 (1998), Controlled Release Society Inc.

Sullivan SA, Meador SK, Carraway KM, Williams JC, Gibson JW, Tipton AJ, Sustained Release of Lysozyme from the SABER Delivery System, AAPS New Orleans, LA, 1999.

Sullivan SA, Meador SK, Dodson Km, Williams JC, Gibson JW, Tipton AJ, Sustained Release of Lysozyme from the SABER Delivery System, Poster, Southern BioSystems, Inc, Birmingham, AL, AAPS New Orleans, LA, 1999.

Smith DA, Tipton AJ, "A novel parenteral delivery system", AAPS—Presentation TDD 7270 Annual Meeting, Seattle, WA (1996).

Tipton AJ, "Sucrose Acetate Isobutyrate (SAIB) for Parenteral Delivery", Reprinted from Modified-Release Drug Delivery Technology, Rathbone, Hadgraft, Roberts (Eds.), 2002 Marcel Dekker, Inc.

Yaxin Lu, et al., "Sucrose Acetate Isobutyrate as an InSitu Forming System for Sustained Risperidone Release", J. Pharm. Sci., vol. 96, No. 12, Dec. 2007, 3252-3262.

Yaxin Lu, et al., "In vivo evaluation of Risperidone-SAIB in situ system as a sustained release delivery system in rats", Eur. J. Pharma and Biopharm, 68 (2008) 422-429.

English language translation of Office Action dated Jun. 15, 2012, from Japanese Application No. 2008-533726, which is a family member of the present application.

Okumu FW, Daugherty A, Sullivan SA, Tipton AJ, Cleland JL; "Evaluation of SABER TM as a local delivery system for rhVEGF-formulation design and in vitro assessment" 2000.

Okumu FW, Dao Le, Fielder PJ, Dybdal N, Brooks D, Sane S. Cleland JL; "Sustained dekivery of human growth hormone from a novel gel system: SABER TM", Bimaterials 23 (2002) 4353-4358.

Middleton JC, Yarbrough JC; "The effect of PEG end groups on the degradation of a 75/25 poly (DL-lactide-co-glycolide", Society for Biomaterials 1999.

Erickson NM, Kines PP, Meador SK, Middleton JC, Williams CT, Williams JC, "An in Vitro Degradation study comparing poly (DL-lactide-co-glycolide) with acid end groups and ester end groups", 20th Southern Biomedical Engineering Conference 2001.

Communication of a Notice of Opposition, Notice of Opposition and Opponents Grounds of Opposition, from EP 2361609, dated May 7, 2014.

Hatefi, et al. "Biodegradable injectable in situ forming drug delivery systems", *Journal of Controlled Release*, vol. 80, pp. 9-28 (2002).

Hou H, etal., *China Med. Press* pp. 223-226, 2011.

"Relday: First once-monthly subcutaneous risperidone for the management of schizophrenia," partnering overview, 2013.

Sinha & Trehan, "Biodegradable Microspheres for Parenteral Delivery", *Critical Reviews in Therapeutic Drug Carrier Systems*, 22(6): 535-602 (2005).

Wang, et al., "Synthesis, characterization, biodegration, and drug delivery application of biodegradable lactic/glycolic acid polymers: I. Synthesis and characterization," *J. Biomater. Sci Polymer Edn*, vol. 11, No. 3, pp. 301-318 (2000).

http://www.absorbables.com/technical/inherent_viscosity.html, published online 2013.

* cited by examiner

DEPOT FORMULATIONS

RELATED APPLICATIONS

The present application is a Continuation of application Ser. No. 12/152,764, filed May 16, 2008, which is a Non-Provisional of Provisional Application No. 60/930,739, filed May 18, 2007. The disclosure of application Ser. No. 12/152,764 is expressly incorporated by reference herein its entirety.

BACKGROUND OF THE INVENTION

Field of the Invention

The invention relates to formulations comprising non-polymeric, non-water soluble high viscosity liquid carrier materials, linear polymers and one or more solvents. More particularly, the invention relates to such formulations and their use in biologically active substance delivery.

Description of Related Art

There has been extensive research in the area of biodegradable controlled release systems for bioactive compounds. Biodegradable matrices for drug delivery are useful because they obviate the need to remove the drug-depleted device.

The most common matrix materials for drug delivery are polymers.

The field of biodegradable polymers has developed rapidly since the synthesis and biodegradability of polylactic acid was reported by Kulkarni et al., in 1966 ("Polylactic acid for surgical implants," Arch. Surg., 93:839). Examples of other polymers which have been reported as useful as a matrix material for delivery devices include polyanhydrides, polyesters such as polyglycolides and polylactide-co-glycolides, polyamino acids such as polylysine, polymers and copolymers of polyethylene oxide, acrylic terminated polyethylene oxide, polyamides, polyurethanes, polyorthoesters, polyacrylonitriles, and polyphosphazenes. See, for example, U.S. Pat. Nos. 4,891,225 and 4,906,474 to Langer (polyanhydrides), U.S. Pat. No. 4,767,628 to Hutchinson (polylactide, polylactide-co-glycolide acid), and U.S. Pat. No. 4,530,840 to Tice, et al. (polylactide, polyglycolide, and copolymers).

Degradable materials of biological origin are well known, for example, crosslinked gelatin. Hyaluronic acid has been crosslinked and used as a degradable swelling polymer for biomedical applications (U.S. Pat. No. 4,957,744 to Della Valle et al.; (1991) "Surface modification of polymeric biomaterials for reduced thrombogenicity," Polym. Mater. Sci. Eng., 62:731-735).

Biodegradable hydrogels have also been developed for use in controlled drug delivery as carriers of biologically active materials such as hormones, enzymes, antibiotics, antineoplastic agents, and cell suspensions. Temporary preservation of functional properties of a carried species, as well as the controlled release of the species into local tissues or systemic circulation, have been achieved. See for example, U.S. Pat. No. 5,149,543 to Cohen. Proper choice of hydrogel macromers can produce membranes with a range of permeability, pore sizes and degradation rates suitable for a variety of applications in surgery, medical diagnosis and treatment.

Many dispersion systems are currently in use as, or being explored for use as, carriers of substances, particularly biologically active compounds. Dispersion systems used for pharmaceutical and cosmetic formulations can be categorized as either suspensions or emulsions. Suspensions are defined as solid particles ranging in size from a few nanometers up to hundreds of microns, dispersed in a liquid medium using suspending agents. Solid particles include microspheres, microcapsules, and nanospheres. Emulsions are defined as dispersions of one liquid in another, stabilized by an interfacial film of emulsifiers such as surfactants and lipids. Emulsion formulations include water in oil and oil in water emulsions, multiple emulsions, microemulsions, microdroplets, and liposomes. Microdroplets are unilamellar phospholipid vesicles that consist of a spherical lipid layer with an oil phase inside, as defined in U.S. Pat. Nos. 4,622,219 and 4,725,442 issued to Haynes. Liposomes are phospholipid vesicles prepared by mixing water-insoluble polar lipids with an aqueous solution. The unfavorable entropy caused by mixing the insoluble lipid in the water produces a highly ordered assembly of concentric closed membranes of phospholipid with entrapped aqueous solution.

U.S. Pat. No. 4,938,763 to Dunn, et al., discloses a method for forming an implant in situ by dissolving a non-reactive, water insoluble thermoplastic polymer in a biocompatible, water soluble solvent to form a liquid, placing the liquid within the body, and allowing the solvent to dissipate to produce a solid implant. The polymer solution can be placed in the body via syringe. The implant can assume the shape of its surrounding cavity. In an alternative embodiment, the implant is formed from reactive, liquid oligomeric polymers which contain no solvent and which cure in place to form solids, usually with the addition of a curing catalyst.

U.S. Pat. No. 5,747,058 to Tipton et al., discloses a composition for the controlled release of substances that includes: (i) a non-polymeric, non-water soluble liquid carrier material (HVLCM) of viscosity of at least 5,000 cP at 37.degree. C. that does not crystallize neat under ambient or physiological conditions; and (ii) a substance to be delivered.

While a number of materials have been evaluated for use in the controlled delivery of substances, there remains a need for formulations and methods that provide controlled delivery of biologically active substances with low toxicity.

BRIEF SUMMARY OF THE INVENTION

In an aspect, the invention relates to formulations comprising: (i) a non-polymeric, non-water soluble high viscosity liquid carrier material having a viscosity of at least 5,000 cP at 37° C. that does not crystallize neat under ambient or physiological conditions; (ii) a linear polymer comprising lactide repeat units, wherein the linear polymer possesses a ratio R of lactide repeat units to total repeat units in the linear polymer; and (iii) one or more solvents that have a solvent capacity; wherein the linear polymer has a weight average molecular weight less than or equal to about 15,000 Daltons, and wherein (a) R satisfies the following: about $0.55 \leq R \leq$ about 0.95; (b) when R satisfies the following: about $0.55 \leq R \leq 0.85$, the solvent capacity of the one or more solvents is greater than or equal to about 20%; and (c) when R satisfies the following: greater than about 0.85 to about 0.95, the solvent capacity of the one or more solvents is greater than or equal to about 10%.

In another aspect, the invention relates to formulations comprising: (i) a non-polymeric, non-water soluble high viscosity liquid carrier material having a viscosity of at least 5,000 cP at 37° C. that does not crystallize neat under ambient or physiological conditions; (ii) a linear polymer comprising lactide repeat units, wherein the linear polymer possesses a ratio R of lactide repeat units to total repeat units in the linear polymer; and (iii) one or more solvents that have a solvent capacity; wherein the linear polymer has a weight average molecular weight less than or equal to about 15,000 Daltons, and wherein: (a) R satisfies the following: about 0.55≤R≤0.85; and (b) the solvent capacity of the one or more solvents is greater than or equal to about 20%.

In yet another aspect, the invention relates to formulations comprising: (i) a non-polymeric, non-water soluble high viscosity liquid carrier material having a viscosity of at least 5,000 cP at 37° C. that does not crystallize neat under ambient or physiological conditions; (ii) a linear polymer comprising lactide repeat units, wherein the linear polymer possesses a ratio R of lactide repeat units to total repeat units in the linear polymer; and (iii) one or more solvents that have a solvent capacity; wherein the linear polymer has a weight average molecular weight less than or equal to about 15,000 Daltons, and wherein (a) R satisfies the following: greater than about 0.85 to about 0.95; and (b) the solvent capacity of the one or more solvents is greater than or equal to about 10%.

In still another aspect, the invention relates to formulations comprising: (i) a non-polymeric, non-water soluble high viscosity liquid carrier material having a viscosity of at least 5,000 cP at 37° C. that does not crystallize neat under ambient or physiological conditions; (ii) a linear polymer comprising lactide repeat units, wherein the linear polymer possesses a ratio R of lactide repeat units to total repeat units in the linear polymer, wherein R satisfies the following: about 0.55≤R≤about 0.95; and (iii) one or more solvents present in an amount ranging from about one weight percent up to about 35 weight percent, based on the total weight of the formulation; wherein the linear polymer has a weight average molecular weight less than or equal to about 15,000 Daltons, and wherein the one or more solvents comprise ethanol, ethyl lactate, propylene carbonate, glycofurol, N-methylpyrrolidone, 2-pyrrolidone, benzyl benzoate, caprylic/capric triglyceride, propylene glycol, acetone, methyl acetate, ethyl acetate, methyl ethyl ketone, benzyl alcohol, triacetin, dimethylformamide, dimethylsulfoxide, tetrahydrofuran, caprolactam, decylmethylsulfoxide, oleic acid, and/or 1-dodecylazacycloheptan-2-one, and combinations of any of the above.

DETAILED DESCRIPTION OF THE INVENTION

Before describing the present invention in detail, it is to be understood that this invention is not limited to particularly exemplified materials or process parameters as such may, of course, vary. It is also to be understood that the terminology used herein is for the purpose of describing particular embodiments of the invention only, and is not intended to be limiting.

All publications, patents and patent applications cited herein, whether supra or infra, are hereby incorporated by reference in their entirety for all purposes.

As used in this specification and the appended claims, the singular forms "a," "an" and "the" include plural referents unless the content clearly dictates otherwise. For example, reference to "a polymer" includes a mixture of two or more such molecules, reference to "a solvent" includes a mixture of two or more such compositions, reference to "an adhesive" includes mixtures of two or more such materials, and the like.

A. Introduction

Surprisingly, the inventors have found that the problems in the art may be addressed by providing formulations that comprise: (i) a non-polymeric, non-water soluble high viscosity liquid carrier material having a viscosity of at least 5,000 cP at 37° C. that does not crystallize neat under ambient or physiological conditions; (ii) a linear polymer comprising lactide repeat units, wherein the linear polymer possesses a ratio R of lactide repeat units to total repeat units in the linear polymer; and (iii) one or more solvents that have a solvent capacity; wherein the linear polymer has a weight average molecular weight less than or equal to about 15,000 Daltons, and wherein (a) R satisfies the following: about 0.55≤R≤about 0.95; (b) when R satisfies the following: about 0.55≤R≤0.85, the solvent capacity of the one or more solvents is greater than or equal to about 20%; and (c) when R satisfies the following: greater than about 0.85 to about 0.95, the solvent capacity of the one or more solvents is greater than or equal to about 10%.

Surprisingly, the inventors further have found that the problems in the art may be addressed by providing formulations that comprise: (i) a non-polymeric, non-water soluble high viscosity liquid carrier material having a viscosity of at least 5,000 cP at 37° C. that does not crystallize neat under ambient or physiological conditions; (ii) a linear polymer comprising lactide repeat units, wherein the linear polymer possesses a ratio R of lactide repeat units to total repeat units in the linear polymer; and (iii) one or more solvents that have a solvent capacity; wherein the linear polymer has a weight average molecular weight less than or equal to about 15,000 Daltons, and wherein: (a) R satisfies the following: about 0.55≤R≤0.85; and (b) the solvent capacity of the one or more solvents is greater than or equal to about 20%.

Additionally surprisingly, the inventors have found that the problems in the art may be addressed by providing formulations that comprise: (i) a non-polymeric, non-water soluble high viscosity liquid carrier material having a viscosity of at least 5,000 cP at 37° C. that does not crystallize neat under ambient or physiological conditions; (ii) a linear polymer comprising lactide repeat units, wherein the linear polymer possesses a ratio R of lactide repeat units to total repeat units in the linear polymer; and (iii) one or more solvents that have a solvent capacity; wherein the linear polymer has a weight average molecular weight less than or equal to about 15,000 Daltons, and wherein (a) R satisfies the following: greater than about 0.85 to about 0.95; and (b) the solvent capacity of the one or more solvents is greater than or equal to about 10%.

In addition, surprisingly, the inventors have found that the problems in the art may be addressed by providing formulations that comprise: (i) a non-polymeric, non-water soluble high viscosity liquid carrier material having a viscosity of at least 5,000 cP at 37° C. that does not crystallize neat under ambient or physiological conditions; (ii) a linear polymer comprising lactide repeat units, wherein the linear polymer possesses a ratio R of lactide repeat units to total repeat units in the linear polymer, wherein R satisfies the following: about 0.55≤R≤about 0.95; and (iii) one or more solvents present in an amount ranging from about one weight percent up to about 35 weight percent, based on the total weight of the formulation; wherein the linear polymer has a weight average molecular weight less than or equal to about 15,000 Daltons, and wherein the one or more solvents comprise ethanol, ethyl lactate, propylene carbonate, glycofurol, N-methylpyrrolidone, 2-pyrrolidone, benzyl benzoate, caprylic/capric triglyceride, propylene glycol, acetone, methyl acetate, ethyl acetate, methyl ethyl ketone, benzyl alcohol, triacetin, dimethylformamide, dimethylsulfoxide, tetrahydrofuran, caprolactam, decylmethylsulfoxide, oleic acid, and/or 1-dodecylazacycloheptan-2-one, and combinations of any of the above.

Linear polymers according to the invention can be used to alter the release profile of the biologically active substance to be delivered, to add integrity to the formulation, or to otherwise modify the properties of the formulation. Such linear polymers according to the invention comprise lactide repeat units. An example of such a polymer is poly(lactide-co-glycolide). The ratio R, which is the ratio of lactide repeat units to total repeat units in the linear polymer, is given in the "R column" of Table 1.

An important consideration in development of formulations according to the invention is the miscibility or solubility of the polymer in the formulation with the HVLCM. In situations where the polymer is not miscible or soluble in the formulation with the HVLCM, phase separation of the polymer and the HVLCM may occur. Once this occurs, it may be very difficult to remix the polymer and the HVLCM, especially at the point of use. Should improper remixing of the formulation occur, it might not release drug in a desired manner. Additionally, the formulations might be difficult to administer. Accordingly, formulations that have high miscibility or solubility of the polymer in the formulation with the HVLCM are desirable.

The inventive formulations possess this high miscibility or solubility of the linear polymer in the formulation with the HVLCM. As can be seen by inspecting Table 1, not all formulations comprising linear polymers, HVLCMs, and solvents result in useful formulations. The formulations listed as "Comparative Formulations" are examples of formulations that were not considered to be useful in the context of the present invention. In contrast, the inventive embodiments, such as those exemplified in Table 1, are useful and exhibit little if any phase separation.

The effect of solvent capacity can be seen, for instance, by examining Formulation 6, which exhibits acceptable solubility behavior. This Formulation comprises 55 wt % sucrose acetate isobutyrate (SAIB), 25 wt % NMP, and 20 wt % of a poly(lactide-co-glycolide) (PLGA) having an R of 0.65 and a Mw of 5300. Formulation 6 has a solvent capacity of 25 wt %. By way of comparison, Formulations C11 and C12 are also presented. Formulation C11 comprises 55 wt % sucrose acetate isobutyrate (SAIB), 20 wt % NMP, 5 wt % of DMSO, and 20 wt % of a poly(lactide-co-glycolide) (PLGA) having an R of 0.65 and a Mw of 5300. Likewise, Formulation C12 comprises 55 wt % sucrose acetate isobutyrate (SAIB), 20 wt % NMP, 5 wt % of benzyl benzoate, and 20 wt % of a poly(lactide-co-glycolide) (PLGA) having an R of 0.65 and a Mw of 5300. Formulations C11 and C12 comprise less than 25 wt % NMP, and are inadequate with respect to their solubility performance. Therefore, the formulations C11 and C12 do not meet the solvent capability requirements and are thus not inventive embodiments of the present invention.

Another way of understanding solvent capacity is shown in Examples 7 and 8. These Examples show how it is possible to determine the solvent capacity for the inventive formulations. This is performed for two additional solvent systems, besides the baseline NMP solvent system, and in two different embodiments of the inventive formulations.

Examples 9 and 10 show embodiments of the inventive formulations that comprise biologically active substances.

The invention will now be described in more detail.

Definitions

All percentages are weight percent unless otherwise noted.

All references cited herein are incorporated herein by reference in their entirety and for all purposes to the same extent as if each individual publication or patent or patent application was specifically and individually indicated to be incorporated by reference in its entirety for all purposes and/or reproduced fully herein. The discussion of references herein is intended merely to summarize the assertions made by their authors and no admission is made that any reference constitutes prior art. Applicants reserve the right to challenge the accuracy and pertinence of the cited references.

The present invention is best understood by reference to the following definitions, the drawings and exemplary disclosure provided herein.

"Administering" or "administration" means providing a drug to a subject in a manner that is pharmacologically useful.

"Biologically active substance" means molecule(s) including a drug, peptide, protein, carbohydrate (including monosaccharides, oligosaccharides, and polysaccharides), nucleoprotein, mucoprotein, lipoprotein, synthetic polypeptide or protein, or a small molecule linked to a protein, glycoprotein, steroid, nucleic acid (any form of DNA, including cDNA, or RNA, or a fragment thereof), nucleotide, nucleoside, oligonucleotides (including antisense oligonucleotides), gene, lipid, hormone, mineral supplement, vitamin including vitamin C and vitamin E, or combinations of any of the above, that cause(s) a biological effect when administered in vivo to an animal, including but not limited to birds and mammals, including humans.

Drug means any substance used internally or externally as a medicine for the treatment, cure, or prevention of a disease or disorder, and includes but is not limited to immunosuppressants, antioxidants, anesthetics, chemotherapeutic agents, steroids (including retinoids), hormones, antibiotics, antivirals, antifungals, antiproliferatives, antihistamines, anticoagulants, antiphotoaging agents, melanotropic peptides, nonsteroidal and steroidal anti-inflammatory compounds, antipsychotics, and radiation absorbers, including UV-absorbers.

The term biologically active substance also includes agents such as insecticides, pesticides, fungicides, rodenticides, and plant nutrients and growth promoters.

In one embodiment, the formulation is a vaccine and the substance to be delivered is an antigen. The antigen can be derived from a cell, bacteria, or virus particle, or portion thereof. As defined herein, antigen may be a protein, peptide, polysaccharide, glycoprotein, glycolipid, nucleic acid, or combination thereof, which elicits an immunogenic response in an animal, for example, a mammal, bird, or fish. As defined herein, the immunogenic response can be humoral or cell-mediated. In the event the material to which the immunogenic response is to be directed is poorly antigenic, it may be conjugated to a carrier such as albumin or to a hapten, using standard covalent binding techniques, for example, with one of the several commercially available reagent kits.

Examples of preferred antigens include viral proteins such as influenza proteins, human immunodeficiency virus (HIV) proteins, and hepatitis A, B, or C proteins, and bacterial proteins, lipopolysaccharides such as gram negative bacterial cell walls and *Neisseria gonorrhea* proteins, and parvovirus.

Non-limiting examples of pharmacological materials include anti-infectives such as nitrofurazone, sodium propionate, antibiotics, including penicillin, tetracycline, oxytetracycline, chlorotetracycline, bacitracin, nystatin, streptomycin, neomycin, polymyxin, gramicidin, chloramphenicol, erythromycin, and azithromycin; sulfonamides, including sulfacetamide, sulfamethizole, sulfamethazine, sulfadiazine, sulfamerazine, and sulfisoxazole, and anti-virals including idoxuridine; antiallergenics such as antazoline, methapyritene, chlorpheniramine, pyrilamine prophenpyridamine, hydrocortisone, cortisone, hydrocortisone acetate, dexamethasone, dexamethasone 21-phosphate, fluocinolone, triamcinolone, medrysone, prednisolone, prednisolone 21-sodium succinate, and prednisolone acetate; desensitizing agents such as ragweed pollen antigens, hay fever pollen antigens, dust antigen and milk antigen; vaccines such as smallpox, yellow fever, distemper, hog cholera, chicken pox, antivenom, scarlet fever, dyptheria toxoid, tetanus toxoid, pigeon pox, whooping cough, influenzae rabies, mumps, measles, poliomyelitic, and Newcastle disease; decongestants such as phenylephrine, naphazoline, and tetrahydrazoline; miotics and anticholinesterases such as pilocarpine, esperine salicylate, carbachol, diisopropyl fluorophosphate, phospholine iodide, and demecarium bromide; parasympatholytics such as atropine sulfate, cyclopentolate, homatropine, scopolamine, tropicamide, eucatropine, and hydroxyamphetamine; sympathomimetics such as epinephrine; sedatives and hypnotics such as pentobarbital sodium, phenobarbital, secobarbital sodium, codeine, (a-bromoisovaleryl)urea, carbromal; psychic energizers such as 3-(2-aminopropyl)indole acetate and 3-(2-aminobutyl)indole acetate; tranquilizers such as reserpine, chlorpromayline, and thiopropazate; androgenic steroids such as methyltestosterone and fluorymesterone; estrogens such as estrone, 17-.beta.-estradiol, ethinyl estradiol, and diethyl stilbestrol; progestational agents such as progesterone, megestrol, melengestrol, chlormadinone, ethisterone, norethynodrel, 19-norprogesterone, norethindrone, medroxyprogesterone and 17-.beta.-hydroxy-progesterone; humoral agents such as the prostaglandins, for example PGE.sub.1, PGE.sub.2 and PGF.sub.2; antipyretics such as aspirin, sodium salicylate, and salicylamide; antispasmodics such as atropine, methantheline, papaverine, and methscopolamine bromide; antimalarials such as the 4-aminoquinolines, 8-aminoquinolines, chloroquine, and pyrimethamine, antihistamines such as diphenhydramine, dimenhydrinate, tripelennamine, perphenazine, and chlorphenazine; cardioactive agents such as dibenzhydroflume thiazide, flumethiazide, chlorothiazide, and aminotrate; antipsychotics including typical and atypical antipsychotics, wherein the atypical antipsychotics comprise risperidone, paliperidone, or olanzapine; nutritional agents such as vitamins, natural and synthetic bioactive peptides and proteins, including growth factors, cell adhesion factors, cytokines, and biological response modifiers; together with pharmaceutically acceptable salts and polymorphs of the above.

The biologically active substance is included in the composition in an amount sufficient to deliver to the host animal or plant an effective amount to achieve a desired effect. The amount of biologically active substance incorporated into the composition depends upon the desired release profile, the concentration of biologically active substance required for a biological effect, and the desired period of release of the biologically active substance.

The concentration of biologically active substance in the composition will also depend on absorption, inactivation, and excretion rates of the biologically active substance as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the inventive formulations, and that the concentration ranges set forth herein are exemplary only and are not intended to limit the scope or practice of the claimed invention. The formulations may be administered in one dosage, or may be divided into a number of smaller doses to be administered at varying intervals of time.

The biologically active substance is typically present in the formulations in the range from about 0.5 percent to about 30 percent by weight relative to the total weight of the formulations, and more typically, between approximately 1 percent to about 20 percent by weight, and more. Another preferred range is from about 2 percent to about 10 percent by weight. For very active biologically active substances, such as growth factors, preferred ranges are less than 1% by weight, and less than 0.0001%.

"Formulation" means a pharmaceutical composition useful in the practice of this invention.

"Linear" means a polymer in which the molecules form long chains substantially without branches or cross-linked structures.

"Non-polymeric, non-water soluble high viscosity liquid carrier material having a viscosity of at least 5,000 cP at 37° C. that does not crystallize neat under ambient or physiological conditions" means a high viscosity liquid carrier material ("HVLCM") that is non-polymeric, non-water soluble, and has a viscosity of at least 5,000 cP; preferably at least 10,000, 15,000; 20,000; 25,000 or even 50,000 cP; at 37° C. that does not crystallize neat under ambient or physiological conditions. The term non-water soluble refers to a material that is soluble in water to a degree of less than one percent by weight under ambient conditions.

In a preferred embodiment, the HVLCM significantly decreases in viscosity when mixed with a solvent to form a low viscosity liquid carrier material ("LVLCM") that can be mixed with a substrate for controlled delivery. The LVLCM/substrate composition is typically easier to place in the body than a HVLCM/substrate composition, because it flows more easily into and out of syringes or other implantation means, and can easily be formulated as an emulsion. The LVLCM can have any desired viscosity. It has been found that a viscosity range for the LVLCM of less than approximately 2000 cP, and more particularly less than 1000 cP, is typically useful for in vivo applications.

In a preferred embodiment, sucrose acetate isobutyrate ("SAIB"), a sucrose molecule nominally esterified preferably with two acetic acid and six isobutyric acid moieties, is used as the HVLCM.

SAIB is orally non-toxic and is currently used as to stabilize emulsions in the food industry. It is a very viscous liquid and has an unusual property that there is a dramatic change in viscosity with small additions of heat or with the addition of solvents. It is soluble in a large number of biocompatible solvents. When in solution or in an emulsion, SAIB can be applied via injection or an aerosol spray. SAIB is compatible with cellulose esters and other polymers that can affect the rate of delivery of the substance.

In other embodiments, the HVLCM can be stearate esters such as those of propylene glycol, glyceryl, diethylaminoethyl, and glycol, stearate amides and other long-chain fatty acid amides, such as N,N'-ethylene distearamide, stearamide MEA and DEA, ethylene bistearamide, cocoamine oxide, long-chain fatty alcohols, such as cetyl alcohol and stearyl alcohol, long-chain esters such as myristyl myristate, beheny erucate, and glyceryl phosphates. In a particular embodiment, the HVLCM is acetylated sucrose distearate (Crodesta A-10). Additional materials suitable for use as the HVLCM are disclosed in US Patent Application Publication US 2004/0101557 by Gibson et al.

The amount of HVLCM in a formulation will depend on the desired properties of a formulation and the solvent capacity of the chosen solvent. If the chosen solvent has poor solvent capacity performance, then the actual amount of solvent may be large, with a corresponding reduction in the amount of HVLCM in the formulation. The HVLCM is typically present in controlled delivery compositions in an amount in the range from about 99.5 percent to about 10 percent by weight, more typically, between 95 and 25 percent, and most typically, between 85 and 45, relative to the total weight of the composition.

"Polymer" means a naturally occurring or synthetic compound made up of a linked series of repeat units. Polymer(s) include, but are not limited to, thermoplastic polymers and thermoset polymers. Polymer(s) may comprise linear polymers and/or branched polymers. Polymers may be synthesized from a single species of monomers, or may be copolymers that may be synthesized from more than one species of monomers. In embodiments, polymers according to the invention comprise polymers that comprise lactide repeat units. Polymers according to the invention may also comprise repeat units of other suitable materials, including but not limited to glycolide repeat units, polyethylene glycol repeat units, caprolactone repeat units, valerolactone repeat units, and the like. Initiators for such polymers include but are not limited to diol initiators including 1,6-hexanediol, 1,2-propanediol, 1,3-propanediol, 1,4-butanediol and the like; diol initiators including difunctional poly(ethylene glycol)s (PEGs); monofunctional alcohol initiators including 1-dodecanol, methyl lactate, ethyl lactate and the like; monofunctional PEGs including methoxy(polyethylene glycol) (mPEG); and other initiators including water, glycolic acid, lactic acid, citric acid, and the like. In preferred embodiments, the polymer comprises a biodegradable polymer. In additional preferred embodiments, the polymer comprises a biocompatible polymer. In embodiments, the polymer may be present in amounts ranging from about 1 wt % to about 45 wt %; more preferably, the polymer may be present in amounts ranging from about 5 wt % to about 35 wt %; and yet more preferably the polymer may be present in amounts ranging from about 5 wt % to about 25 wt %, all based on the total weight of the formulation. In other embodiments, the polymer may be present in an amount ranging from about 15 wt % to about 45 wt %; preferably the polymer may be present in amounts ranging from about 15 wt % to about 35 wt %, all based on the total weight of the formulation.

"Repeat units" means residues of monomers that are covalently incorporated into a polymer. In embodiments, lactide repeat units comprise lactide residues. In certain embodiments, glycolide repeat units comprise glycolide residues. In embodiments, a linear polymer may possess a ratio R of lactide repeat units to total repeat units in the linear polymer, wherein R may range from about 0.55 to about 0.95. Ranges of R of particular interest are from about 0.55 to 0.85, and from great than 0.85 to about 0.95. R may be determined experimentally or analytically for each polymer by proton NMR or similar techniques.

"Solvent(s)" means materials that are capable of dissolving other materials. Preferably, solvents used in the practice of the present invention are biocompatible, water miscible and/or water soluble, and/or non-toxic. In embodiments, the biologically active substance may be soluble in the solvent. The solvents used to inject the inventive formulations into animals should not cause significant tissue irritation or necrosis at the site of implantation, unless irritation or necrosis is the desired effect.

The solvent is preferably water miscible and/or water soluble, so that it will diffuse into bodily fluids or other aqueous environment, causing the formulation to assume a more viscous form. Certain solvents that are not water miscible and/or not water soluble may also be used in the practice of the invention. Examples of suitable solvents include but are not limited to ethanol, ethyl lactate, propylene carbonate, glycofurol, N-methylpyrrolidone, 2-pyrrolidone, benzyl benzoate, caprylic/capric triglyceride, propylene glycol, acetone, methyl acetate, ethyl acetate, methyl ethyl ketone, benzyl alcohol, triacetin, dimethylformamide, dimethylsulfoxide, tetrahydrofuran, caprolactam, decylmethylsulfoxide, oleic acid, and/or 1-dodecylazacycloheptan-2-one, and combinations of any of the above; with the proviso that one or more of the above listed solvents may be specifically excluded from the scope of the invention if it is to be disclaimed.

When SAIB is used as the HVLCM, the preferred solvents include ethanol, dimethylsulfoxide, ethyl lactate, ethyl acetate, benzyl alcohol, triacetin, N-methylpyrrolidone, propylene carbonate, and glycofurol. SAIB is not miscible with glycerol, corn oil, peanut oil, 1,2-propanediol, polyethylene glycol (PEG200), super refined sesame oil, and super refined peanut oil. Accordingly, the latter group of solvents are not preferred for use with SAIB.

"Solvent capacity" means amount(s) of the one or more solvents that dissolves the HVLCM and linear polymer in the formulation to the same extent as would a hypothetical amount of N-methylpyrrolidone in the formulation. Solvent capacity is expressed as that hypothetical weight percent of N-methylpyrrolidone in the formulation, based on the total weight of the hypothetical formulation that would contain the N-methylpyrrolidone.

Thus, in an embodiment, a formulation having a solvent capacity of about 20% would have sufficient amounts of one or more solvents to dissolve the HVLCM and linear polymer to the same extent as if about 20% by weight of NMP were added to the formulation instead of the one or more solvents. If NMP were present as the one or more solvents in this embodiment, it would be present in an amount of about 20% by weight, based on the total weight of the formulation. If the one or more solvents were poorer solvents for the HVLCM and linear polymer, then the one or more solvents would be present in an amount greater than about 20% by weight, based on the total weight of the formulation. This is illustrated further in Examples 10 and 11.

In certain embodiments, when R (the ratio of lactide repeat units to total repeat units in the linear polymer) is between about 0.55 to 0.85, the solvent capacity of the one or more solvents is greater than or equal to about 35%, more preferably greater than or equal to about 25%; and still more preferably greater than or equal to about 20%. Likewise, in certain embodiments, when R ranges from greater than 0.85 to about 0.95, the solvent capacity of the one or more solvents is greater than or equal to about 25%, more preferably greater than or equal to about 15%, and still more preferably greater than or equal to about 10%. Decrease in the lower boundary of solvent capacities represents a physical narrowing of the range of claimed formulations. This is because the number of formulations that exhibit satisfactory solubility behavior over the full range of recited solvent capacities decreases as the lower boundary of solvent capacity decreases.

"Subject" is used interchangeably with "individual" and means any human or animal with which it is desired to practice the present invention. The term "subject" does not denote a particular age, and the present systems are thus suited for use with subjects of any age, such as infant, adolescent, adult and senior aged subjects In certain embodiments, a subject may comprise a patient.

"Weight average molecular weight" or "Mw" means the weighted average molecular weight of polymers of interest. It can be expressed at the first moment of a plot of the weight of polymer in each molecular weight range against molecular weight. In certain embodiments, weight-average molecular weight, Number-average molecular weight (Mn), and the molecular weight distribution (MWD=Mw/Mn) may be measured by gel permeation chromatography (GPC). GPC is a column fractionation method wherein polymer molecules in solutions are separated based on their sizes. The separated polymer molecules are observed by a detector to generate the GPC chromatogram, which is a plot of elution volume or time (related to molecular size) versus abundance. The GPC chromatogram may be integrated to determine Mw, Mn, and MWD.

GPC samples of polymer(s) of interest, approximately 50 mg in 10 mL solvent, are filtered through a 0.2 µm Teflon filter before injection into the instrument. Injections of 50-200 µL are made to generate chromatograms. Chromatograms may be generated using various systems. In an embodiment, a system comprises an Agilent LC 1100 using Chemstation software. In another embodiment, a system comprises a Waters 510 pump, a Shimadzu CTO-10A column oven, and a Waters 410 differential refractometer. Data may be recorded directly to a PC via a Polymer Labs data capture unit using Caliber® software. A calibration curve may be generated using polystyrene standards. Mw, Mn, and MWD relative to polystyrene are calculated. Preferred solvents for use in GPC comprise: chloroform, dichlormethane (methylene chloride), and tetrahydrofuran (THF). Preferred different column sets comprise: (1) two Polymer Labs Mixed C columns in series, (2) two Polymer Labs Mixed D columns in series, or (3) two Polymer Labs Mesopore columns in series. Preferred polystyrene calibrants comprise: Polymer Labs Easical PS1 kit, Polymer Labs Easical PS2 kit, Polymer Labs S-L-10 kit.

In embodiments, the weight average molecular weight of polymers useful in the practice of the present invention is less than or equal to about 15,000 Daltons, additionally more preferably less than or equal to about 12,500 Daltons, and yet more preferably less than or equal to about 10,000 Daltons.

Formulations

As noted above, an important consideration in development of formulations according to the invention is the miscibility or solubility of the polymer in the formulation with the HVLCM. In situations where the polymer is not miscible or soluble in the formulation with the HVLCM, phase separation of the polymer and the HVLCM in the formulation may occur. Once this occurs, it may be very difficult to remix the polymer and the HVLCM, especially at the point of use. Should improper remixing occur, undesirably wide variations in release performance might result. Accordingly, formulations that have high miscibility or solubility of the polymer in the formulation with the HVLCM are desirable.

The inventive formulations possess this high miscibility or solubility of the polymer in the formulation with the HVLCM. Other points useful to consider in terms of formulation strategy may include the following. Minimizing total solvent content of the formulations is generally biologically desirable, for instance in an embodiment having a solvent content ranging from about one weight percent up to about 35 wt % solvent, preferably ranging from about one weight percent up to about 30 wt %, and yet more preferably ranging from about one weight percent up to about 25 wt %, based on the total weight of the formulation. In contrast, increasing solvent content can move a HVLCM/linear polymer/solvent composition from phase separation to single phase behavior. The one or more solvents should be biocompatible, which may eliminate some solvents from use in the invention. In an embodiment, the one or more solvents should be good solvents for both the polymer and HVLCM. In an alternate embodiment, the formulation may comprise the HVLCM, the linear polymer, one or more good solvents for the linear polymer and one or more good solvents for the HVLCM, with the resultant formulation being a single phase.

Solubility and phase separation of various HVLVM/linear polymer/solvent formulation may be investigated by visual techniques well known to those skilled in the art. For formulations with significant instability or tendency to phase-separate, the linear polymer may absorb solvent but remain as a separated, very viscous layer or phase in the formulation. Other formulations might be rendered into a uniform clear solution by sufficient heating and mixing. However, when cooled to room temperature, two clear liquid phases may form. Sometimes, the two clear layers may not be easy to detect, thus requiring strong light and a thorough inspection of the formulation to discern the boundary between the two phases. In a number of cases, formulations may appear clear and uniform on initial cooling to room temperature, but when left quiescent at room temperature for a period of several days or greater, the formulations may separate into two phases. For formulations that are at the border of phase separation, the formulation may turn cloudy and sometimes slowly separate into two phases.

A variety of additives can optionally be included in the inventive formulations to modify the properties of the formulations as desired. The additives can be present in any amount that is sufficient to impart the desired properties to the formulations. The amount of additive used will in general be a function of the nature of the additive and the effect to be achieved, and can be easily determined by one of skill in the art.

When present, additive(s) are typically present in the formulations in an amount in the range from about 0.1 percent to about 20 percent by weight, relative to the total weight of the formulation, and more typically, is present in the composition in an amount in the range from about 1, 2, or 5 percent to about 10 percent by weight, relative to the total weight of the formulation. Certain additives, such as buffers, may be present only in small amounts in the relative to the total weight of the formulation.

Another additive for use with the present compositions are non-biodegradable polymers. Non-limiting examples of non-erodible polymers which can be used as additives include: polyacrylates, ethylene-vinyl acetate polymers, cellulose and cellulose derivatives, acyl substituted cellulose acetates and derivatives thereof, non-erodible polyurethanes, polystyrenes, polyvinyl chloride, polyvinyl fluoride, poly(vinyl imidazole), chlorosulphonated polyolefins, and polyethylene oxide.

Preferred non-biodegradable polymers include polyethylene, polyvinyl pyrrolidone, ethylene vinylacetate, polyethylene glycol, cellulose acetate butyrate ("CAB") and cellulose acetate propionate ("CAP").

A further class of additives which can be used in the inventive formulations are natural and synthetic oils and fats. Oils derived from animals or from plant seeds of nuts typically include glycerides of the fatty acids, chiefly oleic, palmitic, stearic, and linolenic. As a rule the more hydrogen the molecule contains, the thicker the oil becomes.

Non-limiting examples of suitable natural and synthetic oils include vegetable oil, peanut oil, medium chain triglycerides, soybean oil, almond oil, olive oil, sesame oil, peanut oil, fennel oil, camellia oil, corn oil, castor oil, cotton seed oil, and soybean oil, either crude or refined, and medium chain fatty acid triglycerides.

Fats are typically glyceryl esters of higher fatty acids such as stearic and palmitic. Such esters and their mixtures are solids at room temperatures and exhibit crystalline structure. Lard and tallow are examples. In general oils and fats increase the hydrophobicity of the formulation, slowing degradation and water uptake.

Another class of additives which can be used in the inventive formulations comprise carbohydrates and carbohydrate derivatives. Non-limiting examples of these compounds include monosaccharides (simple sugars such as fructose and its isomer glucose (dextrose); disaccharides such as sucrose, maltose, cellobiose, and lactose; and polysaccharides.

Other additives, such as preservatives, stabilizers, antioxidants, coloring agents, isotonic agents, humectants, sequesterants, vitamins and vitamin precursors, surfactants and the like, may be added as needed. As preferred examples of preservatives, paraben derivatives are given with methyl paraben and propyl paraben given as most preferred preservatives. As preferred examples of anti-oxidants, butyl hydroxyanisole, butyl hydroxytoluene, propyl gallate, vitamin E acetate, and purified hydroquinone are given with vitamin E acetate and butyl hydroxytoluene given as most preferred anti-oxidants. Given as preferred examples of humectant is sorbitol. Given as preferred examples of sequesterant is citric acid.

Inventive formulations may be made according to a number of methods. In certain embodiments, first combine room temperature solvent(s), room temperature linear polymer and HVLCM heated to 80° C. Next, mix at 60-80° C. for a period of several hours to overnight (8-16 hours) until the formulation is well-mixed. In other embodiments, dissolve the linear polymer in all of the solvent(s). Add hot HVLCM (heated at up to 80° C.). Then, mix at temperature of room temperature to 80° C. for 1 hour to overnight (8-16 hours) until the formulation is well-mixed. In yet other embodiments, dissolve the linear polymer in some of the solvent(s). Mix the remainder of the solvent(s) with the HVLCM. Add hot HVLCM/solvent mixture (heated at up to 80° C.) to the linear polymer/solvent(s) mixture. Then, mix at temperatures that may range from room temperature to 80° C. for 1 hour to overnight (8-16 hours), until the formulation is well-mixed.

Inventive formulations are preferably prepared at temperatures above room temperature. Once mixed, the formulations may be cooled back to room temperature and initially observed for cloudiness (indication of incipient phase separation), the presence of two liquid layers (usually of low to moderate viscosity) or the presence of a viscous layer underneath a less viscous layer. The formulations may then be left at room temperature for a significant period (usually one week or greater) and observed again for cloudiness, separation into two layers of moderate viscosity or the presence of a viscous layer.

Inventive formulations may be administered to subjects using conventional routes of administration, such as injection. Effective amounts of biologically active substances may be incorporated into the inventive formulations so as to achieve a desired pharmacological effect.

While there has been described and pointed out features and advantages of the invention, as applied to present embodiments, those skilled in the medical art will appreciate that various modifications, changes, additions, and omissions in the method described in the specification can be made without departing from the spirit of the invention.

The present invention is not to be limited in terms of the particular embodiments described in this application, which are intended as single illustrations of individual aspects of the invention. Many modifications and variations of this invention can be made without departing from its spirit and scope, as will be apparent to those skilled in the art. Functionally equivalent methods within the scope of the invention, in addition to those enumerated herein, will be apparent to those skilled in the art from the foregoing description. Such modifications and variations are intended to fall within the scope of the appended claims. The present invention is to be limited only by the terms of the appended claims, along with the full scope of equivalents to which such claims are entitled.

The following Examples are meant to be illustrative of the claimed invention, and not limiting in any way.

EXAMPLES

Example 1: Formulation Examples

Various formulation examples according to the invention, together with various comparative formulation examples, were prepared. Information relating to these examples is set forth in Table 1. The polymer synthesis, and formulation techniques for several representative examples have been set forth below. The remaining non-representative examples were prepared using such representative techniques, and with conventionally obtainable modifications to the representative techniques.

Example 2

A 500 mL three-neck round bottom flask, a glass stirrer bearing, a gas joint, and a glass stirring shaft were dried in a glassware oven at 100° C. to remove all traces of moisture. The following materials were transferred to the flask: 179.00 g DL-lactide, 71.00 g of glycolide, and 13.75 g 1,6-hexanediol. The flask was equipped with the stirring shaft with a Teflon paddle, the stirrer bearing, and a gas joint connected to a manifold with vacuum and nitrogen gas supply. The stirrer shaft/bearing was sealed with a rubber balloon and the reaction mixture was evacuated for several minutes and the flask was backfilled with nitrogen gas. The flask was immersed in an oil bath maintained at 150° C. and stirred using an overhead stirrer attached to the shaft/paddle assembly. Once all of the monomer had melted, a charge of stannous 2-ethylhexanoate was added, 0.075 g in a solution of toluene (559 mL of a solution with a concentration of 0.13416 g/mL) was added to the melt. Stirring was continued for 4 hours Next, the temperature of the oil bath was reduced to 115° C., stirring was stopped, and the stirrer shaft/bearing was sealed with a rubber balloon and the reaction mixture was evacuated under full vacuum for 1 hour. The polymer was then poured onto a piece of Teflon film in a glass dish and allowed to cool. The finished polymer was stored protected from ambient moisture in a vacuum oven and/or plastic bags. The resulting polymer had a Mw of 5300 Da as determined approximately by GPC, and an R ratio of 0.65.

Example 3: Formulation 6

PLGA polymer produced according to Example 2 was removed from cold storage & allowed to warm to room temperature. SAIB (in a glass jar) was heated to 80° C. for several hours. 5.69 grams of hot SAIB were poured into a glass jar. Next, 2.59 grams of NMP were dispensed into the glass jar. Next, 2.05 grams of 65/35 PLGA polymer were dispensed into the glass jar. The jar was sealed and fastened to a rotating mixing wheel. The mixing wheel was placed into an 80° C. oven and turned on so that the jar rotated at the outside of a circular path at a rate sufficient to achieve mixing. After two hours of mixing at 80° C., the jar was removed from the mixing wheel and allowed to cool to room temperature. The formulation composition was 55% SAIB, 25% NMP and 20% PLGA. On standing, the formulation remained clear and did not exhibit any evidence of phase separation.

Example 4

A 1 L three-neck round bottom flask, a glass stirrer bearing, a gas joint, and a stirring shaft were dried in a glassware oven at 100° C. to remove all traces of moisture. The following materials were transferred to the flask: 179.00 g DL-lactide, 71.00 g of glycolide, and 2.1 g of water. The flask was equipped with a stirring shaft and a Teflon paddle, a stirrer bearing, and a gas joint connected to a manifold with vacuum and nitrogen gas supply. The stirrer shaft/bearing was sealed and the reaction mixture was evacuated for several minutes and the flask was backfilled with nitrogen gas. This was repeated 4 additional times. The flask was immersed in an oil bath maintained at 159° C. and stirred using an overhead stirrer attached to the shaft/paddle assembly. Once all of the monomer had melted, a charge of stannous 2-ethylhexanoate, 0.1125 g in a solution of toluene, was added to the melt. Stirring was continued for 15 hours. Next, the temperature of the oil bath was reduced to 115° C., stirring was stopped, and the stirrer shaft/bearing was sealed and the reaction mixture was evacuated under full vacuum for 1 hour. The polymer was then poured onto a piece of Teflon film in a glass dish and allowed to cool. The finished polymer was stored protected from ambient moisture in a vacuum oven and/or plastic bags. The resulting polymer had a Mw of 7200 Da as determined approximately by GPC, and an R ratio of 0.65.

Example 5: Comparative Formulation C3

3.28 grams of PLGA polymer made according to Example 4 were dissolved in a mixture of 1.55 grams of DMSO and 1.55 grams of ethanol. 24.98 grams of warm SAIB were added, with a resulting nominal formulation of 10.5% PLGA, 4.9% DMSO, 4.9% ethanol and 79.7% SAIB. The formulation separated into two phases at room temperature. Additional DMSO (3.90 grams) and additional ethanol (2.25 grams) were added to yield a nominal formulation of 8.8% PLGA, 14.5% DMSO, 10.1% ethanol and 66.6% SAIB. The formulation remained separated into two phases.

Example 6: Formulation 6 (Alternate Formulation Methodology)

PLGA polymer produced according to Example 2 was removed from cold storage & allowed to warm to room temperature. 20.36 grams of 65/35 PLGA polymer were dispensed into a glass jar. 25.45 grams of NMP were added to the jar and the jar was sealed. The jar was fastened to a rotating mixing wheel (Glas Col, Terre Haute, Ind.). The mixing wheel was turned on so that the jar rotated at the outside of a circular path, with heating at approximately 80 C until the polymer was dissolved in the NMP. 55.49 grams of SAIB (warmed) were added to the polymer/NMP solution. The jar was sealed and fastened to a rotating mixing wheel (Glas Col, Terre Haute, Ind.). The mixing wheel was turned on so that the jar rotated at the outside of a circular path at a speed sufficient to achieve mixing. The solution was mixed until a uniform preparation was achieved. The formulation composition was 55% SAIB, 25% NMP and 20% PLGA, all expressed as wt % based on total weight of the formulation. On standing, the vehicle remained clear and did not exhibit any evidence of phase separation.

Example 7: Solvent Capacity Experiments

Approximately 2.5 g of PLGA having a molecular weight of 4700 Da, a lactide/glycolide ratio of 65/35, and initiated by hexanediol; and 6.855 g of SAIB were added to a vial (i.e. fixed weight relationship of polymer to SAIB). Solvents, as shown in Table 2 below, were slowly added and the formulation was mixed at 60° C. in a Emprotech Unitherm® oven until a single phase solution was formed. The solution was then removed from the oven and allowed to sit on a bench top at roughly room temperature for approximately a week. If the solution phase separated more solvent was added and the formulation was mixed at 60° C. until a single phase solution was formed and remained a single phase for one week while sitting on the bench top at roughly room temperature. The final compositions are shown in Table as shown in Table 2 below. The solvent capacity of this vehicle was 25.61 wt %. 26.44 wt % wt % of BA or 42.64 wt % of DMSO were needed to achieve that solvent capacity.

TABLE 2

(FIGS. are weight percent of total final weight)

| Material | Trial A | Trial B | Trial C |
|---|---|---|---|
| SAIB | 53.86 | 41.99 | 54.55 |
| PLGA | 19.70 | 15.37 | 19.84 |
| NMP |  |  | 25.61 |
| BA | 26.44 |  |  |
| DMSO |  | 42.64 |  |

Example 8: Solvent Capacity Experiments

Approximately 2.5 g of PLGA having a molecular weight of 6600 Da, a lactide/glycolide ratio of 65/35, and initiated with dodecanol; and 6.855 g of SAIB were added to a vial. Solvents, as shown in Table 3 below, were slowly added and the formulation was mixed at 60° C. in a Emprotech Unitherm® oven until a single phase solution was formed.

The solution was then removed from the oven and allowed to sit on a bench top at roughly room temperature for approximately a week. If the solution phase separated more solvent was added and the formulation was mixed at 60° C. until a single phase solution was formed and remained a single phase for one week while sitting on the bench top at roughly room temperature. The final compositions are shown in Table 3 below. The solvent capacity of this vehicle was 17.36 wt %. 19.70 wt % of BA or 31.22 wt % of DMSO were needed to achieve that solvent capacity.

TABLE 3

| (FIGS. are weight percent of total final weight) | | | |
|---|---|---|---|
| Material | Trial D | Trial E | Trial F |
| SAIB | 58.83 | 50.37 | 60.58 |
| PLGA | 21.47 | 18.41 | 22.06 |
| NMP | | | 17.36 |
| BA | 19.70 | | |
| DMSO | | 31.22 | |

Example 9: Naltrexone Formulation 0.555 grams of PLGA (65/35 L/G, 1-dodecanol initiated, MW of 6400 Daltons by GPC, from DURECT® Birmingham) was mixed with 3.620 grams of Benzyl Alcohol (from J. T. Baker) in a sealed bottle by gentle inversion inside a Lindberg/Blue M oven at 60° C. for 35 minutes, resulting in homogeneous solution. To this mixture was added 6.094 grams of hot SAIB (from Eastman Chemicals). The vehicle was mixed by gentle inversion for approximately 65 hours at room temperature. A uniform vehicle resulted (SAIB/benzyl alcohol/PLGA 59.34/35.25/5.40). 0.118 grams of naltrexone base (Mallinckrodt) was added to a separate bottle. 4.205 grams of the vehicle was added to this bottle. The naltrexone was dissolved in the vehicle by gentle inversion for approximately 3 hours, resulting in a uniform clear solution that was pale yellow in color. The composition of the naltrexone formulation (in wt % based on total formulation weight) was:

| PLGA: | 5.3% |
|---|---|
| Benzyl alcohol | 34.3% |
| SAIB | 57.7% |
| Naltrexone | 2.7% |

Example 10: Risperidone Formulation

The atypical antipsychotic drug risperidone was added to the formulation of Example 3 (Formulation 26) as follows: To 7.33 grams of Formulation 26, 1.095 grams of risperidone (from Kemprotec) were added. The vial was placed on a Glas-Col rotating wheel set at 30% for approximately two hours until a homogeneous suspension was obtained. The resulting formulation had the composition of 48% SAIB, 22% NMP, 17% PLGA and 13% Risperidone, with percentages expressed as weight percent based on total weight of the formulation. The resulting vehicle was a stable homogeneous suspension.

TABLE 1

| Formulation #: | Polymer | R | Mw (GPC) | Formulation composition | Solubility Behavior |
|---|---|---|---|---|---|
| 1 | PLGA 65/35-COOH | 0.65 | 7200 | SAIB/NMP/EtOH/PLGA-COOH: 68.4/13.2/9.2/9.3 | Soluble |
| 2 | PLGA 65/35 | 0.65 | 5300 | SAIB/NMP/PLGA: 70/25/5 | Soluble |
| 3 | PLGA 65/35 | 0.65 | 5300 | SAIB/NMP/PLGA: 70.3/20.3/9.4 | Soluble |
| 4 | PLGA 65/35 | 0.65 | 5300 | SAIB/NMP/PLGA: 59.7/26.5/13.8 | Soluble |
| 5 | PLGA 65/35 | 0.65 | 5300 | SAIB/NMP/PLGA: 65/30/15 | Soluble |
| 6 | PLGA 65/35 | 0.65 | 5300 | SAIB/NMP/PLGA: 55/25/20 | Soluble |
| 7 | PLGA 65/35 | 0.65 | 5300 | SAIB/NMP/EtOH/PLGA: 58.6/14.0/9.4/18.0 | cloudy but single phase |
| 8 | PLGA 65/35 | 0.65 | 5300 | SAIB/NMP/EtOH/PLGA: 55.0/15.1/10.0/20.0 | Soluble |
| 9 | PLGA 65/35 | 0.65 | 5300 | SAIB/NMP/EtOH/PLGA: 55.1/19.9/5.0/20.0 | Soluble |
| 10 | PLGA 65/35 | 0.65 | 5300 | SAIB/NMP/DMSO/PLGA: 54.1/19.8/6.0/20.1 | Soluble |
| 11 | PLGA 65/35 | 0.65 | 5300 | SAIB/NMP/BA/PLGA: 55/20/5/20 | Soluble |
| 12 | PLGA 65/35 | 0.65 | 5300 | SAIB/DMSO/EtOH/PLGA: 65/25/5/5 | Soluble |
| 13 | PLGA 65/35 | 0.65 | 5300 | SAIB/DMSO/BA/PLGA: 65/25/5/5 | Soluble |
| 14 | PLGA 65/35 | 0.65 | 5300 | SAIB/DMSO/NMP/PLGA: 65/25/5/5 | Soluble |
| 15 | PLGA 65/35 | 0.65 | 4100 | SAIB/NMP/PLGA: 53.1/21.9/25.0 | Soluble |
| 16 | PLGA 65/35 | 0.65 | 4100 | SAIB/NMP/PLGA: 49.2/22.6/28.2 | Soluble |
| 17 | PLGA 65/35 | 0.65 | 4100 | SAIB/NMP/PLGA: 29.7/33.9/36.4 | Soluble |
| 18 | PLGA 65/35 | 0.65 | 3200 | SAIB/NMP/PLGA: 70.0/20.0/10.0 | Soluble |
| 19 | PLGA 65/35 | 0.65 | 4700 | SAIB/NMP/PLGA: 55/25/20 | Soluble |
| 20 | PLGA 65/35 | 0.65 | 6600 | SAIB/NMP/PLGA: 55/25/20 | Soluble |
| 21 | PLGA 65/35 | 0.65 | 6600 | SAIB/NMP/EtOH/PLGA: 55/15/10/20 | Soluble |
| 22 | PLGA 60/40 | 0.6 | 3200 | SAIB/NMP/PLGA: 70.0/20.0/10.0 | Soluble |
| 23 | PLGA 55/45 | 0.55 | 3200 | SAIB/NMP/PLGA: 65/25/10 | Soluble |
| C1 | PLGA 65/35-COOH | 0.65 | 7200 | SAIB/NMP/PLGA-COOH: 70/25/5 | not soluble |
| C2 | PLGA 65/35-COOH | 0.65 | 7200 | SAIB/BA/EtOH/PLGA-COOH: 65.3/14.1/11.1/9.5 | not soluble |
| C3 | PLGA 65/35-COOH | 0.65 | 7200 | SAIB/DMSO/EtOH/PLGA: 66.6/14.5/10.1/8.8 | not soluble |
| C4 | PLGA 65/35 | 0.65 | 5300 | SAIB/NMP/PLGA: 75/15/10 | not soluble |
| C5 | PLGA 65/35 | 0.65 | 5300 | SAIB/NMP/PLGA: 65/20/15 | not soluble |

TABLE 1-continued

| Formulation #: | Polymer | R | Mw (GPC) | Formulation composition | Solubility Behavior |
|---|---|---|---|---|---|
| C6 | PLGA 65/35 | 0.65 | 5300 | SAIB/NMP/PLGA: 60/20/20 | not soluble |
| C7 | PLGA 65/35 | 0.65 | 5300 | SAIB/NMP/EtOH/PLGA: 72.9/8.8/8.6/9.6 | not soluble |
| C8 | PLGA 65/35 | 0.65 | 5300 | SAIB/NMP/EtOH/PLGA: 62.0/17.2/4.6/16.2 | separates long term |
| C9 | PLGA 65/35 | 0.65 | 5300 | SAIB/NMP/DMSO/PLGA: 53.8/15.4/10.8/20.1 | separates long term |
| C10 | PLGA 65/35 | 0.65 | 5300 | SAIB/NMP/DMSO/PLGA: 54.9/15.0/9.8/20.1 | separates long term |
| C11 | PLGA 65/35 | 0.65 | 5300 | SAIB/NMP/DMSO/PLGA: 55/20/5/20 | separates long term |
| C12 | PLGA 65/35 | 0.65 | 5300 | SAIB/NMP/BB/PLGA: 55/20/5/20 | not soluble |
| C13 | PLGA 65/35 | 0.65 | 5300 | SAIB/DMSO/PLGA: 70/25/5 | not soluble |
| C14 | PLGA 65/35 | 0.65 | 5300 | SAIB/DMSO/PLGA: 65/30/5 | not soluble |
| C15 | PLGA 65/35 | 0.65 | 5300 | SAIB/DMSO/EtOH/PLGA: 71.7/10.0/8.7/9.7 | not soluble |
| C16 | PLGA 65/35 | 0.65 | 5300 | SAIB/DMSO/BB/PLGA: 65/25/5/5 | not soluble |
| C17 | PLGA 65/35 | 0.65 | 5300 | SAIB/BA/EtOH/PLGA: 69.8/11.8/8.8/9.5 | not soluble |
| C18 | PLGA 50/50-COOH | 0.50 | 5500 | SAIB/NMP/PLGA-COOH: 70/25/5 | separates at RT & 37 C |

What is claimed is:

1. A formulation comprising:
    a biologically active substance; and
    a vehicle comprising:
        (i) sucrose acetate isobutyrate (SAIB) in an amount of from 25 to 85 wt % based on the total weight of the formulation;
        (ii) a linear poly(lactide-co-glycolide) in an amount of from 10 to 45 wt % based on the total weight of the formulation, wherein the linear poly(lactide-co-glycolide) possesses a ratio R of lactide repeat units to total repeat units in the linear poly(lactide-co-glycolide); and
        (iii) one or more solvents that have a solvent capacity, wherein the one or more solvents dissolve the SAIB and the linear poly(lactide-co-glycolide), and wherein the SAIB, linear poly(lactide-co-glycolide), and one or more solvents are monophasic when maintained at approximately 25° C. for a one-week period;
    wherein the linear poly(lactide-co-glycolide) has a weight average molecular weight less than or equal to 15,000 Daltons, and wherein
        (a) R satisfies the following: 0.55≤R≤about 0.95;
        (b) when R satisfies the following: 0.55≤R≤0.85, the solvent capacity of the one or more solvents is greater than or equal to 25%; and
        (c) when R satisfies the following: greater than 0.85 to about 0.95, the solvent capacity of the one or more solvents is greater than or equal to about 10%.

2. The formulation of claim 1, wherein when R satisfies the following: greater than 0.85 to about 0.95, the solvent capacity of the one or more solvents is greater than or equal to about 15%.

3. The formulation of claim 2, wherein: wherein when R satisfies the following: 0.55≤R≤0.85, the solvent capacity of the one or more solvents is greater than or equal to about 35%; and when R satisfies the following: greater than 0.85 to about 0.95, the solvent capacity of the one or more solvents is greater than or equal to about 25%.

4. The formulation of claim 1, wherein the biologically active substance comprises an atypical antipsychotic.

5. The formulation of claim 4, wherein the atypical antipsychotic comprises risperidone or a pharmaceutically acceptable salt or polymorph thereof.

6. The formulation of claim 1, wherein the linear poly(lactide-co-glycolide) is present in an amount ranging from about 15 wt % to 45 wt %, based on the total weight of the formulation.

7. The formulation of claim 1, wherein when R satisfies the following: greater than 0.85 to about 0.95, the solvent capacity of the one or more solvents is greater than 20%.

8. The formulation of claim 1, wherein the linear poly(lactide-co-glycolide) has a weight average molecular weight less than 12,500 Daltons.

9. A formulation comprising:
    a biologically active substance; and
    a vehicle comprising:
        (i) sucrose acetate isobutyrate (SAIB) in an amount of from 25 to 85 wt % based on the total weight of the formulation;
        (ii) a linear poly(lactide-co-glycolide) in an amount of from 10 to 45 wt % based on the total weight of the formulation, wherein the linear poly(lactide-co-glycolide) possesses a ratio R of lactide repeat units to total repeat units in the linear poly(lactide-co-glycolide); and
        (iii) one or more solvents that have a solvent capacity, wherein the one or more solvents dissolve the SAIB and the linear poly(lactide-co-glycolide), and wherein the SAIB, linear poly(lactide-co-glycolide), and one or more solvents are monophasic when maintained at approximately 25° C. for a one-week period;
    wherein the linear poly(lactide-co-glycolide) has a weight average molecular weight less than or equal to 15,000 Daltons, and
    wherein:
        (a) R satisfies the following: 0.55≤R≤0.85; and
        (b) the solvent capacity of the one or more solvents is greater than or equal to 25%.

10. The formulation of claim 9, wherein the solvent capacity of the one or more solvents is greater than or equal to about 35%.

11. The formulation of claim 9, wherein the biologically active substance comprises an atypical antipsychotic.

12. The formulation of claim 11, wherein the atypical antipsychotic comprises risperidone or a pharmaceutically acceptable salt or polymorph thereof.

13. The formulation of claim 9, wherein the linear poly(lactide-co-glycolide) is present in an amount ranging from about 15 wt % to 45 wt %, based on the total weight of the formulation.

14. The formulation of claim 9, wherein the linear poly(lactide-co-glycolide) has a weight average molecular weight less than 12,500 Daltons.

15. A formulation comprising:
a biologically active substance; and
a vehicle comprising:
(i) sucrose acetate isobutyrate (SAIB) in an amount of from 25 to 85 wt % based on the total weight of the formulation;
(ii) a linear poly(lactide-co-glycolide) in an amount of from 10 to 45 wt % based on the total weight of the formulation, wherein the linear poly(lactide-co-glycolide) possesses a ratio R of lactide repeat units to total repeat units in the linear poly(lactide-co-glycolide); and
(iii) one or more solvents that have a solvent capacity, wherein the one or more solvents dissolve the SAIB and the linear poly(lactide-co-glycolide), and wherein the SAIB, linear poly(lactide-co-glycolide), and one or more solvents are monophasic when maintained at approximately 25° C. for a one-week period;
wherein the linear poly(lactide-co-glycolide) has a weight average molecular weight less than or equal to 15,000 Daltons, and wherein
R satisfies the following: greater than 0.85 to about 0.95; and
the solvent capacity of the one or more solvents is greater than or equal to about 10%.

16. The formulation of claim 15, wherein the solvent capacity of the one or more solvents is greater than or equal to about 15%.

17. The formulation of claim 15, wherein the solvent capacity of the one or more solvents is greater than or equal to about 25%.

18. The formulation of claim 15, wherein the biologically active substance comprises an atypical antipsychotic.

19. The formulation of claim 18, wherein the atypical antipsychotic comprises risperidone or a pharmaceutically acceptable salt or polymorph thereof.

20. The formulation of claim 15, wherein the linear poly(lactide-co-glycolide) is present in an amount ranging from about 15 wt % to 45 wt %, based on the total weight of the formulation.

21. The formulation of claim 15, wherein the solvent capacity is greater than 20%.

22. The formulation of claim 15, wherein the linear poly(lactide-co-glycolide) has a weight average molecular weight less than 12,500 Daltons.

23. A formulation comprising:
a biologically active substance; and
a vehicle comprising:
(i) sucrose acetate isobutyrate (SAIB) in an amount of from 25 to 85 wt % based on the total weight of the formulation;
(ii) a linear poly(lactide-co-glycolide) in an amount of from 10 to 45 wt % based on the total weight of the formulation, wherein the linear poly(lactide-co-glycolide) possesses a ratio R of lactide repeat units to total repeat units in the linear poly(lactide-co-glycolide), wherein R satisfies the following: $0.55 \leq R \leq$ about 0.95; and
(iii) one or more solvents present in an amount ranging from 25 weight percent up to about 35 weight percent, based on the total weight of the formulation, wherein the one or more solvents dissolve the SAIB and the linear poly(lactide-co-glycolide), and wherein the SAIB, linear poly(lactide-co-glycolide), and one or more solvents are monophasic when maintained at approximately 25° C. for a one-week period;
wherein the linear poly(lactide-co-glycolide) has a weight average molecular weight less than or equal to 15,000 Daltons, and
wherein the one or more solvents comprise ethanol, ethyl lactate, propylene carbonate, glycofurol, N-methylpyrrolidone, 2-pyrrolidone, benzyl benzoate, caprylic/capric triglyceride, propylene glycol, acetone, methyl acetate, ethyl acetate, methyl ethyl ketone, benzyl alcohol, triacetin, dimethylformamide, dimethylsulfoxide, tetrahydrofuran, caprolactam, decylmethylsulfoxide, oleic acid, 1-dodecylazacycloheptan-2-one, and combinations thereof.

24. The formulation of claim 23, wherein the biologically active substance comprises an atypical antipsychotic.

25. The formulation of claim 24, wherein the atypical antipsychotic comprises risperidone or a pharmaceutically acceptable salt or polymorph thereof.

26. The formulation of claim 23, wherein the linear poly(lactide-co-glycolide) is present in an amount ranging from about 15 wt % to 45 wt %, based on the total weight of the formulation.

27. The formulation of claim 23, wherein the linear poly(lactide-co-glycolide) has a weight average molecular weight less than 12,500 Daltons.

* * * * *